United States Patent
Grollier et al.

[11] Patent Number: 5,104,643
[45] Date of Patent: Apr. 14, 1992

[54] SHAVING COMPOSITION FOR THE SKIN BASED ON POLYORGANO-SILOXANES CONTAINING A HYDROXYALKYL GROUP AND PROCESS FOR USE

[75] Inventors: Jean F. Grollier, Paris; Alain Caudet, Boulogne-Billancourt, both of France

[73] Assignee: L'Oreal, Paris, France

[21] Appl. No.: 431,027

[22] Filed: Nov. 2, 1989

[30] Foreign Application Priority Data

Nov. 4, 1988 [FR] France ............... 88 14450

[51] Int. Cl.$^5$ .................................. A61K 7/00
[52] U.S. Cl. ........................... 424/47; 424/70; 424/73; 514/63; 514/778
[58] Field of Search .......... 528/32; 424/73, 70, 424/45, 47; 556/416; 514/63, 778; 524/731, 265, 860, 269; 428/403, 405; 521/92

[56] References Cited

U.S. PATENT DOCUMENTS

| | | | |
|---|---|---|---|
| 3,159,601 | 12/1964 | Ashby | 528/32 |
| 4,065,422 | 12/1977 | Lundmark | 424/73 |
| 4,145,411 | 3/1979 | Mende | 424/73 |
| 4,160,775 | 7/1979 | Schilling | 556/416 |
| 4,178,364 | 12/1979 | Rucker | 424/73 |
| 4,185,087 | 1/1980 | Morlino | 424/70 |
| 4,490,356 | 12/1984 | Sebag | 424/70 |
| 4,495,169 | 1/1985 | Schmolka | 424/45 |
| 4,574,052 | 4/1986 | Gupte | 424/45 |
| 4,609,750 | 9/1986 | Kollmeier | 514/63 |
| 4,656,221 | 4/1987 | Kurita | 524/731 |
| 4,849,211 | 7/1989 | Schrauzer | 424/45 |

FOREIGN PATENT DOCUMENTS 1467863  1/1969  Fed. Rep. of Germany .
2443476  7/1980  France .
2066659  7/1981  United Kingdom .

*Primary Examiner*—Thurman K. Page
*Assistant Examiner*—William E. Benston, Jr.
*Attorney, Agent, or Firm*—Marshall, O'Toole, Gerstein, Murray & Bicknell

[57] ABSTRACT

Shaving composition for the skin based on polyorganosiloxanes containing a hydroxyalkyl group and process for use. The present invention relates to a composition intended for shaving of the skin, containing, in a cosmetically acceptable medium containing a foaming agent, a polyorganosiloxane containing a hydroxyl group, of formula I:

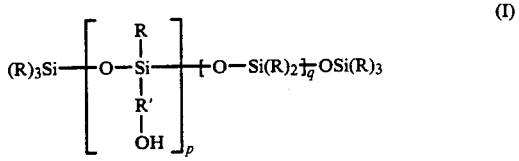

in which the radicals R, which may be identical or different, denote methyl or phenyl, at least 60 mol % of the radicals R being methyl; the radical R' is a divalent linear or branched $C_2$–$C_8$ alkylene group of the hydrocarbon type; p is an integer between 1 and 30 inclusive; q is an integer between 1 and 150 inclusive; and also to a process for using it.

18 Claims, No Drawings

SHAVING COMPOSITION FOR THE SKIN BASED ON POLYORGANO-SILOXANES CONTAINING A HYDROXYALKYL GROUP AND PROCESS FOR USE

The present invention relates to new compositions intended for shaving of the skin, based on polyorganosiloxanes containing a hydroxyalkyl group, and to a process for using them.

Some polyorganosiloxanes are well known in the field of shaving compositions, and are used in formulations for shaving creams, pre-shave lotions and shaving foams. They are chiefly volatile silicones such as polydimethylsiloxane or "dimethicone", or polydimethylcyclosiloxane or "cyclomethicone".

These silicones, used in shaving compositions, have the function of alleviating shaving rash as a result of their lubricating power, of making the skin softer and more satiny and of making the compositions containing them rather agreeable to use.

However, these silicones are also known for their antifoam property, and are difficult to use in shaving foams packaged as aerosols. When these silicones permit foam formation, the foam generally varies greatly in quality and stability according to the extent of filling of the aerosol container.

Applicants discovered, surprisingly, that the use of polyorganosiloxanes containing hydroxyalkyl group in shaving compositions enabled a substantial improvement to be obtained in the smoothness and softness of these compositions, in addition to the properties stated above for silicones.

Applicants also discovered that the use of these polyorganosiloxanes containing a hydroxyalkyl group in shaving foams enabled the latter to preserve their quality during the gradual emptying of the aerosol container.

Finally, Applicants discovered that compositions according to the invention, containing polyorganosiloxanes containing a hydroxyalkyl group, improved the cutting of the hairs during shaving, were removed very readily from both the skin and razor blades on rinsing with water, and rapidly left the skin clean and satiny.

A subject of the invention consists of the compositions intended for shaving of the skin, containing polyorganosiloxanes containing a hydroxyalkyl group.

The subject of the invention is also a process for shaving the skin employing these compositions.

Other subjects of the invention will become apparent on reading the description and the examples which follow.

The subject of the present invention is hence a composition intended for shaving of the skin, containing, in a cosmetically acceptable medium, a foaming agent and at least one polyorganosiloxane containing a hydroxyalkyl group, corresponding to the following formula (I):

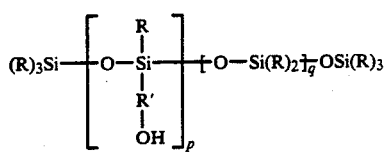

(I)

in which:
the radicals R, which may be identical or different, are selected from methyl and phenyl radicals, at least 60 mol% of the radicals R being methyl radicals;

the radical R' is a divalent linear or branched alkylene group of the hydrocarbon type containing from 2 to 18 carbon atoms;

p is an integer between 1 and 30 inclusive, and preferably between 1 and 20 inclusive; and q is an integer between 1 and 150 inclusive.

The copolymer according to the invention can be an alternating or random copolymer.

Among especially preferred compounds used according to the invention, compounds of formula (I) in which:

R' denotes a divalent linear or branched alkylene group of the hydrocarbon type containing 2 to 6 carbon atoms, and more especially a trimethylene chain, —CH$_2$)$_3$, or a 2-methyltrimethylene group,

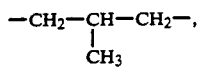

may be used.

Among the products of formula (I), it is preferable to use products whose number average molecular mass is between 600 and 10,000.

Preferred products of formula (I) are represented by the products of number average molecular mass between 1,000 and 10,000 for which p is between 1 and 5 and q is between 10 and 120.

Still more especially, products of formula (I) of molecular mass between 8,000 and 10,000 for which p is between 1 and 3 and q between 100 and 120, and among these the compounds of formula (I) in which R denotes a methyl radical and R' denotes a trimethylene radical —(CH$_2$)$_3$—, are preferred.

The products of formula (I) are known per se, and may be prepared according to known processes of the prior art, such as those described in French Patent No. 85/16,334 and U.S. Pat. Nos. 2,970,150 and 4,160,775.

To prepare the products of formula (I), it is possible, for example, to use as starting organopolysiloxanes the copolymer of formula (II):

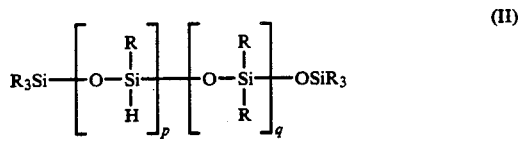

(II)

in which R, p and q have the meaning given above.

The products of formula (II) are well known in the silicone industry and are generally available on the market. They are, for example, described in U.S. Pat. Nos. 3,220,942, 3,341,111 and 3,436,366.

The products of formula (II) are reacted with an alkenically unsaturated alcohol of formula (III):

in which R" is a linear or branched alkenyl radical having from 2 to 18 carbon atoms.

Among these alcohols, allyl alcohol and methallyl alcohol are used more especially.

As a hydrosilylation catalyst for reacting the unsaturated alcohols of formula (III) with the hydrogenopolysiloxane of formula (II), it is possible to use known hydrosilylation catalysts, in particular the platinum complexes described in U.S. Pat. Nos. 3,715,334, 3,775,452 and 3,814,730; and the platinum/olefin complexes described in U.S. Pat. Nos. 3,159,601 and 3,159,662.

The cosmetically acceptable medium according to the present invention is an aqueous medium containing at least one foaming agent.

The foaming agent according to the present invention is selected from foaming synthetic anionic surfactants, or soaps consisting of $C_8$–$C_{20}$ fatty acids neutralized with an alkaline agent such as triethanolamine, potassium hydroxide, sodium hydroxide or mixtures thereof.

The anionic surfactants used according to the present invention are preferably selected from alkali metal and ammonium salts of N-acylglutamic, alkylisethionic, alkylsulphosuccinic and alkylsulphoacetic acids, of N-acylsarcosine and of N-acyl-N-methyltaurine, the alkyl and acyl radicals containing 14 to 22 carbon atoms.

The fatty acids used according to the present invention preferably consist of mixtures of $C_{16}$–$C_{20}$ fatty acids and $C_8$–$C_{20}$ fatty acids, and in particular mixtures of stearic acid and coconut fatty acid or of stearic acid and myristic acid or alternatively of stearic acid and lauric acid.

The proportion in soap of $C_{16}$–$C_{20}$ fatty acids is between 40 and 90%, and preferably between 75 and 90%, by weight relative to the total weight of the quantity of soap; and that in soap of $C_8$–$C_{20}$ fatty acids from 10 to 60%, and preferably from 10 to 25%, by weight relative to the total weight of the quantity of soap.

Other foaming agents may be used in combination with the fatty acid soaps or the foaming anionic surfactants defined above, such as, for example, nonionic, amphoteric or anionic surfactant agents different from those mentioned above, or polymers such as polyvinyl alcohol.

Preferred compositions according to the invention contain from 10 to 85% by weight of water, and from 0.5 to 80% by weight of soap consisting of $C_8$–$C_{20}$ fatty acids neutralized with an alkaline agent or anionic surfactants as defined above.

The compositions for shaving the skin according to the invention contain, in the cosmetically acceptable medium defined above, a polyorganosiloxane containing a hydroxyalkyl group of the formula (I) in concentrations of between 0.2 and 3% by weight, and preferably between 0.5 and 2% by weight, relative to the total weight of the composition.

These compositions may be presented in the form of creams, gels, self-foaming gels, solid soaps and aerosol foams.

The shaving compositions according to the invention may be packaged as aerosols and distributed in the form of foams or self-foaming gels.

In this case, the composition is used in the presence of a propellent gas, selected from volatile hydrocarbons such as n-butane, isobutane and propane, of which a ternary mixture of n-butane, isobutane and propane sold, for example, by the company ELF AQUITAINE under the name AEROGAZ 3,2 N is preferred more especially, or partially or completely fluorinated hydrocarbons including, more especially, monofluorotrichloromethane, dichlorodifluoromethane (F12) and 1,2-dichloro-1,1,2,2-tetrafluoroethane (F114), used alone or in combination; chlorinated and/or fluorinated hydrocarbons of this type are sold under the name of Fréon or Dymel by the company DU PONT DE NEMOURS. It is also possible to use as a propellant mixtures of these volatile hydrocarbons with chlorinated and/or fluorinated hydrocarbons, such as, for example, a mixture of n-butane, isobutane, propane and monofluorotrichloromethane, or propellants such as nitrous oxide, carbon dioxide or dimethyl ether.

More especially preferred shaving compositions according to the invention are represented by aerosol foams containing from 75 to 85% by weight of water, from 0.5 to 15% by weight of soap or anionic surfactant as described above, from 0.2 to 3% by weight of a polyorganosiloxane of formula (I), in which R' denotes —$CH_2)_3$, of number average molecular mass between 8,000 and 10,000 and for which p is between 1 and 3 and q between 100 and 120, and from 2 to 15%, and more especially from 3 to 10%, by weight of a propellant agent.

The compositions according to the invention can contain, in addition to the polyorganosiloxane of formula (I), adjuvants customarily used in the field of shaving compositions, such as moisturizing agents selected from sorbitol and glycerol, transparency agents also playing the part of solvents, such as glycols, for example propylene glycol or ethylene glycol, film-forming agents, emollients such as, for example, lanolin derivatives or cationic polymers or polyethylene glycols, skin treatment agents such as antiacne and antiseborrhoeic agents, mineral oils, fatty alcohols, polymers, thickeners, stabilizing agents such as, for example, ethanolamides, soothing agents such as allantoin, camphor and methanol, anionic surfactants other than soaps or those defined above, nonionic or amphoteric surfactants or mixtures thereof, colourings, preservatives, antioxidants and fragrances.

The process for shaving the skin according to the present invention consists essentially in applying a composition as defined above to the skin, in shaving the latter by means of a mechanical razor and in following this by rinsing with water.

The examples which follow are designed to give a better illustration of the invention without, however, limiting the latter.

EXAMPLE 1

An aerosol shaving foam of the following composition is prepared:

| | |
|---|---|
| Stearic acid | 8.0 g |
| Coconut fatty acid | 1.0 g |
| Potassium hydroxide | 0.5 g |
| Triethanolamine | 3.0 g |
| Polysiloxane of formula: | 1.0 g |

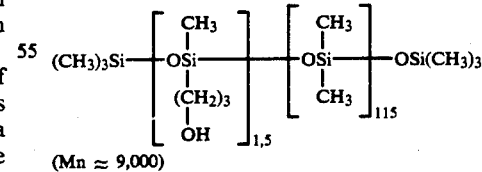

(Mn ≈ 9,000)

| | |
|---|---|
| Glycerol | 4.0 g |
| Isopropanolamine salts of myristic acid, sold under the name LANAMINE by the company AMERCHOL | 2.0 g |
| Polyoxyethyleneated sorbitan monolaurate containing 20 moles of ethylene oxide, sold under the name TWEEN 20 by the company ATLAS | 0.5 g |
| Fragrance | qs |
| Water | qs 100.0 g |

| -continued | |
|---|---|
| Aerosol packaging: | |
| Above composition | 96.0 g |
| Propellant: | 4.0 g |
| Ternary mixture of n-butane, isobutane >55% and propane, sold under the name AEROGAZ 3,2 N by the company ELF AQUITAINE | |
| Total | 100.0 g |

EXAMPLE 2

An aerosol shaving foam of the following composition is prepared:

| | |
|---|---|
| Stearic acid | 5.5 g |
| Myristic acid | 1.2 g |
| Potassium hydroxide | 0.4 g |
| Triethanolamine | 3.3 g |
| Glycerol | 2.5 g |
| Polysiloxane of formula: | 1.0 g |

$$(CH_3)_3Si-\left[OSi\begin{array}{c}CH_3\\|\\|\\(CH_2)_3\\|\\OH\end{array}\right]_{1,5}-\left[OSi\begin{array}{c}CH_3\\|\\|\\CH_3\end{array}\right]_{115}-OSi(CH_3)_3$$

(Mn ≈ 9,000)

| | |
|---|---|
| Lanolic acid | 0.5 g |
| Amphoteric surfactant known as "Cocoamphocarboxyglycinate" (CTFA, 3rd edition, 1982), sold under the name MIRANOL C2M Conc by the company MIRANOL, in aqueous solution containing 38% of active substance | 0.2 g AS |
| Dimethyldiallylammonium/acrylamide copolymer, sold by the company MERCK in aqueous solution containing 8% of active substance (AS) under the name MERQUAT S | 0.25 g AS |
| Fragrance qs | |
| Water | qs 100.0 g |
| Aerosol packaging: | |
| Above composition | 92.0 g |
| Propellant: Fréons 12/114 (53:47) | 8.0 g |
| Total | 100.0 g |

EXAMPLE 3

A self-foaming shaving gel of the following composition is prepared:

| | |
|---|---|
| Stearic acid | 5.0 g |
| Palmitic acid | 5.0 g |
| Triethanolamine | 5.5 g |
| Polysiloxane of formula: | 0.5 g |

$$(CH_3)_3Si-\left[OSi\begin{array}{c}CH_3\\|\\|\\(CH_2)_3\\|\\OH\end{array}\right]_{1,5}-\left[OSi\begin{array}{c}CH_3\\|\\|\\CH_3\end{array}\right]_{115}-OSi(CH_3)_3$$

(Mn ≈ 9,000)

| | |
|---|---|
| Polyethylene glycol, sold by the company UNION CARBIDE under the name POLYOX WSR 205 | 0.55 g |
| Polyethylene glycol ether (20 EO) of oleyl alcohol, sold by the company ICI AMERICAS under the name BRIJ 98 | 2.0 g |
| Hydroxyethylcellulose, sold by the company UNION CARBIDE under the name CELLOSIZE | |
| PCG 10 | 1.4 g |
| Sorbitol | 1.0 g |
| Fragrance, colouring qs | |
| Water | 100 g |

96 g of this composition are introduced into the central part of a double-walled aerosol can, the inner wall of which consists of an impermeable compressible membrane separating the propellant (outer jacket) from the self-foaming gelled composition (central part).

4 g of an isopentane/Fréon 114 mixture (60:40) are then introduced into the central part. After the valve is fitted, the aerosol can is pressurized by introducing 10% of a ternary mixture of n-butane, isobutane >55% and propane, sold under the name AEROGAZ 3,2 N by the company ELF AQUITAINE, into the jacket.

When applied to the skin, this gel develops a foam very rapidly.

EXAMPLE 4

A shaving cream of the following composition is prepared:

| | |
|---|---|
| Stearic acid | 34.0 g |
| Coconut fatty acid | 8.5 g |
| Potassium hydroxide | 7.5 g |
| Sodium hydroxide | 0.75 g |
| Glycerol | 13.5 g |
| Polysiloxane of formula: | 2.0 g |

$$(CH_3)_3Si-\left[OSi\begin{array}{c}CH_3\\|\\|\\(CH_2)_3\\|\\OH\end{array}\right]_{1,5}-\left[OSi\begin{array}{c}CH_3\\|\\|\\CH_3\end{array}\right]_{115}-OSi(CH_3)_3$$

(Mn ≈ 9,000)

| | |
|---|---|
| Antioxidant, fragrance qs | |
| Water | qs 100.0 g |

EXAMPLE 5

A shaving foam of the following composition is prepared:

| | |
|---|---|
| Sodium N-methyloleyltaurinate, sold by the company GAF under the name FENOPON TK 42 at a concentration of 32% AS (active substance) | 4.8 g AS |
| Sodium lauryl ether sulphate containing 70% AS | 2.1 g AS |
| Sorbitol containing 70% AS | 5.6 g AS |
| Lanolic acid | 0.5 g |
| Polyoxyethylenated sorbitan monolaurate containing 20 moles of ethylene oxide, sold by the company ATLAS under the name TWEEN 20 | 0.5 g |
| Dimethyldiallylammonium chloride/acrylamide copolymer, sold by the company GAF in aqueous solution containing 8% AS under the name MERQUAT S | 0.08 g AS |
| Polysiloxane of formula: | 2.0 g |

$$(CH_3)_3Si-\left[OSi\begin{array}{c}CH_3\\|\\|\\(CH_2)_3\\|\\OH\end{array}\right]_{1,5}-\left[OSi\begin{array}{c}CH_3\\|\\|\\CH_3\end{array}\right]_{115}-OSi(CH_3)_3$$

-continued

| | | |
|---|---|---|
| (Mn ≈ 9,000) | | |
| Hydroxyethylcellulose, sold by the company UNION CARBIDE under the name CELLOSIZE PCG 10 | | 1.5 g |
| D-Panthenol, in solution containing 50% AS | | 0.375 g AS |
| Colouring, fragrance qs | | |
| Water | qs | 100.0 g |
| Aerosol packaging: | | |
| Above composition | | 94.0 g |
| Propellant: Isobutane | | 6.0 g |
| | Total | 100.0 g |

EXAMPLE 6

A shaving foam of the following composition is prepared:

| | |
|---|---|
| Monosodium salt of N-acylglutamic acid of formula: | 4.0 g |

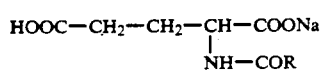

where R is a mixture of tallow fatty acid-derived $C_{14}$-$C_{22}$ hydrogenated alkyl and/or alkenyl radicals, sold under the name ACYLGLUTAMATE HS 11 by the company AJINOMOTO

| | |
|---|---|
| Disodium salt of N-acylglutamic acid of the above formula, sold under the name ACYLGLUTAMATE HS 21 by the company AJINOMOTO | 3.0 g |
| Glycerol | 3.0 g |
| Lanolic acid | 1.0 g |
| Amphoteric surfactant known as "Cocoamphocarboxyglycinate" (CTFA, 3rd edition, 1982) sold under the name MIRANOL C2M Conc by the company MIRANOL, in aqueous solution containing 38% of active substance (AS) | 0.38 g AS |
| Hydroxyethylcellulose, sold by the company UNION CARBIDE under the name CELLOSIZE PCG 10 | 1.0 g |
| Polyethylene glycol, sold by the company UNION CARBIDE under the name POLYOX WSR 205 | 0.5 g |
| Polyethylene glycol, sold by the company UNION CARBIDE under the name POLYOX COAGULANT | 0.05 g |
| Polysiloxane of formula: | 1.0 g |

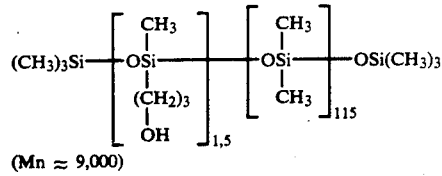

(Mn ≈ 9,000)

| | | |
|---|---|---|
| Fragrance qs | | |
| Water | qs | 100.0 g |
| Aerosol packaging: | | |
| Above composition | | 96.0 g |
| Propellant: Ternary mixture of n-butane, isobutane >55% and propane, sold by the company ELF AQUITAINE under the name AEROGAZ 3,2 N | | 4.0 g |
| | TOTAL | 100.0 g |

We claim:

1. Composition intended for shaving of the skin, which contains, in an aqueous medium, an effective amount for producing a shave foam of a soap consisting of a $C_8$-$C_{20}$ fatty acid neutralized with an alkaline agent or an anionic surfactant and an effective amount, for improving the cutting of the hairs during shaving and after shaving for making the skin softer and more satiny, of a polyorganosiloxane containing a hydroxyalkyl group, corresponding to the following formula (I):

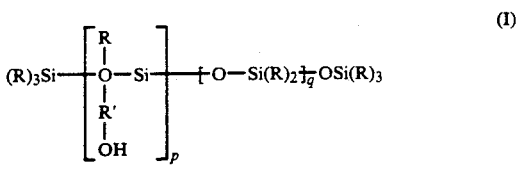

in which the radicals R, which may be identical or different, are selected from methyl and phenyl radicals, at least 60 mol % of the radicals R being methyl radicals; the radical R' is a divalent linear or branched alkylene group of the hydrocarbon type containing from 2 to 18 carbon atoms; p is an integer between 1 and 30 inclusive; and q is an integer between 1 and 150 inclusive.

2. Composition according to claim 1, in which, in the compounds of formula (I), R' denotes a divalent linear or branched alkylene group of the hydrocarbon type containing from 2 to 6 carbon atoms.

3. Composition according to claim 1, in which, in the compounds of formula (I), R' is a trimethylene radical, $-CH_2)_3$, or a 2-methyltrimethylene group,

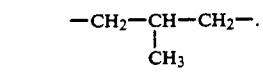

4. Composition according to claim 1, in which, in the compounds of formula (I), R denotes a methyl radical, R' a trimethylene radical, p is an integer between 1 and 3 and q is an integer between 100 and 120, these compounds having a number average molecular mass of between 8,000 and 10,000.

5. Composition according to claim 1, which contains in a cosmetically acceptable medium containing a foaming agent, a polyorganosiloxane of formula (I), in concentrations of between 0.2 and 3% by weight, relative to the total weight of the composition.

6. Composition according to claim 1, wherein the cosmetically acceptable medium consists of water, and wherein the foaming agent is a soap consisting of a $C_8$-$C_{20}$ fatty acid neutralized with an alkaline agent or a synthetic anionic surfactant.

7. Composition according to claim 6, wherein the anionic surfactant agent is selected from alkali metal and ammonium salts of N-acylglutamic, alkylisethionic, alkylsulphosuccinic and alkylsulphoacetic acids, of N-acylsarcosine and of N-acyl-N-methyltaurine, the alkyl and acyl radicals containing 14 to 22 carbon atoms.

8. Composition according to claim 1, wherein the foaming agent is a soap consisting of a mixture of $C_8$-$C_{20}$ fatty acids, wherein the proportion of $C_8$-$C_{20}$ fatty acids is between 10 and 60%, relative to the total weight of the quantity of soap, and wherein the proportion of $C_{16}$-$C_{20}$ fatty acids is between 40 and 90%, by weight relative to the total weight of the quantity of soap.

9. Composition according to claim 1, which contains from 10 to 85% by weight of water and from 0.5 to 80% by weight of a soap consisting of a $C_8$-$C_{20}$ fatty acid neutralized with an alkaline agent or a synthetic anionic surfactant.

10. Composition according to claim 1, which contains in addition, a foaming polymer or a nonionic, amphoteric or anionic foaming surfactant agent which is not a member of the group consisting of alkali metal and ammonium salts of N-acylglutamic, alkylisethionic, alkylsulphosuccinic and alkylsulphoacetic acids, of N-acylsarcosine and of N-acyl-N-methyltaurine, the alkyl and acyl radicals containing 14 to 22 carbon atoms.

11. Composition according to claim 1, which is packaged as an aerosol in the presence of a propellant gas, so as to form a self-forming gel or a foam at the time of expulsion.

12. Composition according to claim 11, in the form of an aerosol which composition contains 75 to 85% by weight of water, 0.5 to 15% by weight of a soap consisting of a $C_8$-$C_{20}$ fatty acid nautralized with an alkaline agent or a synthetic anionic surfactant, 0.2 to 3% by weight of an organopolysiloxane of formula (I) and from 2 to 15% by weight of a propellant gas, relative to the total weight of the composition.

13. Composition according to claim 1, which contains, in addition, moisturizing agents, transparency agents, film-forming agents, emollients, anti-acne and antiseborrhoeic agents, mineral oils, fatty alcohols, polymers, thickeners, stabilizing agents, soothing agents, anionic surfactants other than soaps or, alkali metal or ammonium salts of N-acylglutamic, alkylisethionic, alkylsulphosuccinic or alkylsulphoacetic acids, of N-acylsarcosine and of N-acyl-N-methyltaurine, the alkyl and acyl radicals containing 14 to 22 carbon atoms, nonionic or amphoteric surfactants or mixtures thereof, colorings, preservatives, antioxidants and fragrances.

14. Process for shaving the skin, wherein a composition as defined in claim 1 is applied to the skin, the skin is shaved by means of a mechanical razor and is rinsed with water.

15. A composition according to claim 13 containing 3 to 10% by weight of said propellant gas.

16. Composition according to claim 5 containing between 0.5 and 2% by weight of said polyorganosiloxane.

17. Composition according to claim 8 wherein the proportion of said $C_8$-$C_{20}$ fatty acids is between 10 and 25%.

18. Composition according to claim 12 containing 3 to 10% by weight of said propellent gas.

* * * * *